US005686246A

United States Patent [19]
Kornman et al.

[11] Patent Number: 5,686,246
[45] Date of Patent: Nov. 11, 1997

[54] DETECTING GENETIC PREDISPOSITION TO PERIODONTAL DISEASE

[76] Inventors: Kenneth S. Kornman, 3007 Orchard Hill, San Antonio, Tex. 78230; Gordon W. Duff, 18 Ashgate Road, Broomhill, Sheffield, England, S10 3BC

[21] Appl. No.: 510,696

[22] Filed: Aug. 3, 1995

[51] Int. Cl.[6] .................. C12Q 1/68; C12P 19/34; C07H 21/04

[52] U.S. Cl. ............. 435/6; 435/91.2; 435/810; 536/23.5; 536/24.31; 536/24.33; 436/63; 935/77; 935/78; 935/8

[58] Field of Search ............... 435/6, 91.2, 810; 536/24.33, 24.31, 23.5; 436/63; 935/77, 78, 8

[56] References Cited

U.S. PATENT DOCUMENTS

| | | | |
|---|---|---|---|
| 4,582,788 | 4/1986 | Erlich | 435/6 |
| 4,666,828 | 5/1987 | Gusella | 435/6 |
| 4,738,927 | 4/1988 | Taniguchi et al. | 435/243 |
| 4,772,685 | 9/1988 | Schmidt et al. | 530/326 |
| 4,801,531 | 1/1989 | Frossard | 435/6 |
| 4,992,367 | 2/1991 | Cullen | 435/69.52 |
| 5,110,920 | 5/1992 | Erlich | 536/27 |
| 5,158,871 | 10/1992 | Rossomando et al. | 435/7.32 |
| 5,206,344 | 4/1993 | Katre et al. | 530/351 |
| 5,215,895 | 6/1993 | Bennett et al. | 435/69.52 |
| 5,268,267 | 12/1993 | Smith | 435/6 |
| 5,272,057 | 12/1993 | Smulson et al. | 435/6 |
| 5,328,829 | 7/1994 | Stashenko | 435/7.9 |

OTHER PUBLICATIONS

Blakemore et al., "Interleukin–1 receptor antagonist gene polymorphism as a disease severity factor in systemic *Lupus erythematosus*" *Arthritis and Rheumatism* 37(9):1380–1385 (1994).
Clark et al., "Genomic sequence for human prointerleukin 1 beta: possible evolution. . ." *Nucl Acid Res*, 14:7897–7914 (1986) [published erratum appears in Nucleic Acids Res., 15(2):868 (1987)].
de Giovine et al., "Single base polymorphism at—511 in the human interleukin–1β gene (IL1β)" *Human Molecular Genetics* 1, No. 6:450 (1992).
Duff, "Cytokines and anti-cytokines" *Br. J. Rheumatol.* 32 (Suppl 1):15–20 (1993).
Furutani et al., "Complete nucleotide sequence of the gene for human interleukin 1 alpha" *Nucl Acids Res.*, 14:3167–3179 (1986).
Mansfield et al., "Novel genetic association between ulcerative colitis and the anti-inflammatory cytokine interleukin 1 receptor . . ." *Gastroenterology*, 106:637–642 (1994).
McDowell et al., "A genetic association between juvenile rheumatoid arthritis and a novel interleukin–1α polymorphism" *Arthritis & Rheumatism*, vol. 38, No. 2, pp. 221–228 (1995).
McGuire et al., "Variation in the TNF–α promoter region associated with susceptibility to cerebral malaria" *Nature*, 371:508–511 (1994).

Michalowicz et al. "Periodontal findings in adult twins" *J Periodontol*, 62:293–299 (1991).
Oppenheim et al., "Cytokines" Basic and Clinical Immunology, 8th ed., eds Stites, Terr & Parslow Chaper 9, pp. 105–123 (1994).
Verjans et al., "Polymorphism of the tumor necrosis factor region in relation to disease: an overview" *Rheum Dis Clin North Am*, 18:177–186 (1992).
Wilson et al., "Single base polymorphism in the human tumour necrosis factor alpha (TNFα) gene . . ." *Human Molecular Genetics 1*, No. 5:353 (1992).
Woolf, "On estimating the relationship between blood group and disease" *Annals of Human Genetics*, 19:251–253 (1955).
Anusaksathien, O. and A.E. Dolby, "Autoimmunity in periodontal disease", *J. Oral Pathol. Med.*, 20:101–1–7 (1991).
Anusaksathien, O. et al., "Autoimmunity to collagen in adult periodontal disease: Immunoglobulin classes in sera and tissue", *J. Periodont. Res.*, 27:55–61 (1992).
Dalboge, H. et al., "Cloning and expression of an interleukin–1–β precursor and its conversion to interleukin–1β", *FEBS Letters*, 246:89–93 (1989).
Hirsch, H.Z. et al., "Autoimmunity to collagen in adult periodontal disease", *J. Oral Path.*, 17(9):456–459 (1988).
Jandinski, J.J. et al., "Localization of interleukin 1α and tumor necrosis factor α in human gingiva", *J. Dental Res.*, 68 (Special Issue), Abstract #526 (1989).
Jandinski, J.J. et al., "Localization of interleukin 1–beta in human periodontal tissue", *J.Periodontol.*, 18:703–707 (1991).
Jonsson, R. et al., "Immunoglobulin isotype distribution of locally produced autoantibodies to caollagen type I in adult periodontitis", *J. Clin. Periodontol.*, 18:703–707(1991).
Kjeldsen, M. et al., "Marginal Periodontitis and Cytokines: A Review of the Literature", *J. Periodontol.*, 64(11):1013–1022 (1993).
Lamster, L.B. et al., "Host Mediators in Gingival Crevicular Fluid: Implications for the Pathogenesis of Periodontal Disease", *Critical Rev. in Oral Biol. and Med.*, 3(1/2):31–60 (1992).
Masada, M.P. et al., "Measurement of interleukin–1 alpha and –1 beta in gingival crevicular fluid: implications for the pathogenesis of periodontal disease", *J. Period. Res.*, 25(3): 156–163 (1990).
Pociot, F. et al., "A TaqI polymorphism in the human interleukin 1–β (1L–1β) gene correlates with 1L–1β secretion in vitro", *Eur. J. Clin. Invest.*, 22(396–402) (1992).
Ranney, R.R., "Immunological mechanisms of pathogenesis in periodontal diseases: An assessment", *J. Period. Res.*, 26:243–254 (1991).

(List continued on next page.)

*Primary Examiner*—Carla J. Myers
*Attorney, Agent, or Firm*—Jenkens & Gilchrist, P.C.

[57] ABSTRACT

A method and kit for the identification of a patient's genetic polymorphism pattern associated with increased periodontal disease severity is disclosed. The kit includes DNA sample collecting means and means for determining a genetic polymorphism pattern which is then compared to control samples to determine a patient's susceptibility to severe periodontal disease.

9 Claims, No Drawings

OTHER PUBLICATIONS

Snyderman, R. and G.A. McCarty, "Analogous mechanisms of tissue destruction in rheumatoid arthritis and periodontal disease", *In: Host Parasite Interactions in Periodontal Disease*, Eds. R.J. Genco and S.E. Mergenhagen, American Society for Microbiology, Washington, D.C. (1982).

Sosroseno, W. et al., "The Interleukin Network in the Immunopathogenesis of Oral Diseases", *Asian Pacific J. Allergy and Immunol.*, 156:296–309 (1994).

Takeichi, O. et al., "Human Polymorphonuclear Leukocytes Derived from Chronically Inflamed Tissue Express Inflammatory Cytokines in vivo", *Cellular Immunol.*, 156: 269–309 (1994).

Wilton, J.M. et al., "Interleukin–1 beta and IgG subclass concentrations in gingival crevicular fluid from patients with adult periodontitis", *Arch Oral Biol.*, 38(1):55–60 (1993).

Wilton, J.M.A. et al., "Interleukin–1 beta (1L–1β) levels in gingival crevicular fluid from adults with previous evidence of destructive periodontitis", *J. Clin. Periodontol.* 19(1)53–57 (1992).

DETECTING GENETIC PREDISPOSITION TO PERIODONTAL DISEASE

BACKGROUND OF THE INVENTION

1. Technical Field

This invention relates to a method of detecting a predisposition for severity of periodontal disease.

2. Background Art

Periodontal disease is a disease of the hard and soft tissues that support the teeth and is initiated by oral bacteria. Gingivitis is an early stage of the periodontal disease where the gums may become red, swollen and bleed easily. Gingivitis is usually painless and, if not treated, can advance to periodontitis, which may be classified by the magnitude of tissue destruction as mild, moderate, or severe. Periodontitis is primarily a disease of adults and is usually not detectable until after the age of 35.

Bacteria that are present in dental plaque initiate periodontal disease. Toxins produced by the bacteria in the plaque activate the body's inflammatory and other immune mechanisms which ultimately leads to the destruction of the bone and gum tissue that support the teeth. As the disease progresses, the gums pull away from the teeth and periodontal pockets are formed which provide a protected environment for the bacteria, thereby causing the cycle to continue. However, some sites do not continue to be active. U.S. Pat. No. 5,328,829 discloses a method for determination of active periodontal disease sites within the oral cavity by measuring interleukin IL-1β at the site. Smoking has been associated with an increased prevalence and severity of periodontitis. However, a significant number of individuals with periodontitis have never smoked.

For the past 15 years, there has been evidence that certain forms of periodontitis that affect young children and teenagers are genetically determined. These diseases, which are of extremely low prevalence in the population, produce severe periodontitis in some individuals before the age of puberty and in other individuals between puberty and age 18. The genetic factors that were identified in those cases involved very overt biologic mechanisms that most likely would predispose the individual to multiple health problems. To date, efforts to find the same types of genetic factors in adult forms of periodontitis have not been successful.

In spite of the above failures, new evidence emerged beginning in 1990 from studies of identical twins that indicated that genetics play a significant role in the clinical presentation of disease in adult forms of periodontitis (Michalowicz et al., 1991). While the twin studies indicated that there was a genetic component, it was not identified. It would be useful to determine patients who are susceptible to severe adult periodontitis.

Genetic testing is now possible (see U.S. Pat. Nos. 4,582,788 and 5,110,920) for diseases associated with or caused by one to two genes, once the genes are identified, to determine the risk of a person carrying a given gene for the disease (see for example U.S. Pat. Nos. 4,801,531, 4,666, 828 and 5,268,267).

As with any infection, once initiated, inflammatory and other immune mechanisms of the body come into play (see U.S. Pat. No. 5,328,829, column 1, for a review). In general, research on inflammatory markers has had very limited success at differentiating periodontitis disease severity and there have been limited and unsuccessful efforts directed to the genetic aspects of the inflammatory response of periodontal disease. Genetic variation at the multiple loci controlling the inflammatory and other immune responses in selected diseases with inflammatory components has been a factor in determining susceptibility to, or severity of, disease. Therefore, it was an objective of the present invention to determine if genetic factors that are associated with inflammatory and other immune responses are correlated with periodontal disease severity. If so, it would be useful to identify the genetic factors and thereby identify patients who are susceptible to severe forms of adult periodontal disease.

SUMMARY OF THE INVENTION

According to the present invention a method for predicting increased periodontal disease severity is disclosed. The method includes the steps of isolating DNA from a patient and determining the DNA polymorphism pattern of the genes that code for IL-1α and IL-1β. The identified pattern is compared to controls of known disease severity thereby identifying patients expressing a genetic polymorphism pattern associated with increased periodontal disease severity.

Patients so identified can then be treated more aggressively in the early stages of periodontal disease to prevent the occurrence of severe disease.

The present invention further discloses a kit for the identification of a patient's genetic polymorphism pattern associated with increased periodontal disease severity. The kit includes DNA sample collecting means and means for determining a genetic polymorphism pattern, which is then compared to control samples to determine a patient's susceptibility to severe periodontal disease.

DETAILED DESCRIPTION OF THE PREFERRED EMBODIMENT

According to the present invention, patients with or without overt disease are identified as having a genetic predisposition for severe periodontal disease by detecting the presence of a DNA polymorphism in the gene sequence for interleukins IL-1α and IL-1β. Severe periodontal disease is defined as set forth in the example herein below. Briefly, severe disease is defined as patients presenting with a history of ≧10 interproximal sites that measure ≧7 mm, with pocket depth (PD) of ≧7 man occurring on at least eight teeth. In addition, clinical attachment (CAL) measured ≧5 mm on ≧11 sites is seen. The definition further requires that full mouth radiographs taken within the last three years shows ≧7 interproximal sites with ≧50% bone loss on radiographs with a total mouth mean bone loss greater than 30%.

The alleles associated with severe disease were identified as IL-1A allele 2 together with IL-1B (TaqI) allele 2. It was determined that the Odds Ratio (OR) for severe periodontitis is 4.3 for patients carrying at least one copy of IL-1A allele 2 and IL-1B (TaqI) allele 2 among nonsmokers. In a population of smokers and nonsmokers the OR for a smoker or patients carrying at least one copy of IL-1A allele 2 and IL-1B (TaqI) allele 2 is 10.06 for having severe disease.

Further, according to the present invention, a kit for the identification of a patient's genetic polymorphism pattern associated with increased periodontal disease severity is disclosed. The kit includes DNA sample collecting means and means for determining a genetic polymorphism pattern for IL-1A and IL-1B, which pattern is then compared to control samples to determine a patient's susceptibility to severe periodontal disease.

The DNA sample is obtained from blood or tissue samples. In a preferred embodiment, the DNA will be obtained from blood cells obtained from a finger prick of the patient with the blood collected on absorbent paper. In a further preferred embodiment, the blood will be collected on an AmpliCard™ (University of Sheffield, Department of Medicine and Pharmacology, Royal Hallamshire Hospital, Sheffield, England S10 2JF). The DNA is then isolated from the dried blood spots and then target sequences amplified using the polymerase chain reaction (PCR). Oligonucleotide DNA primers that target the specific polymorphic DNA region within the genes of interest are prepared so that in the PCR reaction amplification of the target sequences is achieved. This embodiment has the advantage of requiring only a small amount of blood and avoids the necessity for venipuncture or a tissue biopsy. However, other means for collecting DNA and determining polymorphism patterns as known in the art can be used.

The amplified DNA sequences from the template DNA are then analyzed using restriction enzymes to determine the genetic polymorphisms present in the amplified sequences and thereby provide a genetic polymorphism profile of the patient.

Some diseases have prominent inflammatory and other immune components. One of the primary components of the inflammatory and other immune responses is cytokine production. Cytokines are peptide/protein immunomodulators that are produced by activated immune cells including thymus-derived T lymphocytes (T-cells), B lymphocytes and monocyte/macrophages. The cytokines include interleukins (IL-1 through IL-15), colony stimulating factors (CSFs) for granulocytes and/or macrophages (CSF-G, CSF-M, CSF-GM), tumor necrosis factors (TNFs $\alpha$ & $\beta$), and interferons (IFN $\alpha$, $\beta$ & $\gamma$). The basic activity of IL-1 includes the combined activities of IL-1$\alpha$, IL-1$\beta$ and IL-1 receptor antagonist (IL-1ra). (For a review, see Duff, 1993; and *Basic and Clinical Immunology*, 8th Ed., 1994, Stites, Terr & Parslow, editors, Chapter 9, pgs. 105–123.). U.S. Pat. No. 5,328,829 found IL-1$\beta$ at active sites in periodontal disease but did not report any correlation with disease state. Association of a single cytokine polymorphism and disease states have been found as, for example, in Systemic Lupus Erythematosus, Ulcerative Colitis and Juvenile rheumatoid arthritis (Mansfield et al., 1994; Verjans et al., 1992; Blakemore et al., 1994; McGuire et al., 1994; McDowell et al., 1995).

Specific polymorphisms in DNA sequences coding for cytokines IL-1$\alpha$ and IL-1$\beta$ were found to be associated with severe periodontal disease. The polymorphisms are as follows:

IL-1A: (Chromosome 2 at 2q12-14)

The alleles of a bi-allelic polymorphism of a single base variation (C/T) at −889 are identified by allele-specific cleavage using a restriction enzyme. The gene is designated IL-1A while the product (cytokine) is designated IL-1$\alpha$. Allele 1 is C and allele 2 is T at base −889. The full restriction enzyme recognition site is created by introducing a partial site by mutation in the PCR reaction with a modified primer sequence. The site is completed by the sequence of one of the alleles of the polymorphism. After restriction enzyme digestion of the products of the PCR reaction, the DNA is separated electrophoretically by size.

From this gel (or a southern blot of it probed with a radioactive internal DNA sequence) the alleles of the polymorphism are identified. The uncut fragment (larger) is the rarer allele in Northern European populations.

IL-1B: (Chromosome 2; 2q12-14)

Two bi-allelic polymorphisms can be typed in two different PCR products using allele-specific cleavage at naturally-occurring sites in the alleles. Allele identification is by size of fragment after restriction digestion and separation in an agarose gel. The gene is designated IL-1B while the product (cytokine) is designated IL-1$\beta$. The sites are single base variations (C/T) at −511 (referred to as IL-1B (AvaI)) and at +3953 (referred to as IL-1B (TaqI)) and are identified by allele-specific cleavage using restriction enzymes. For each polymorphism allele 1 is C and allele 2 is T.

The patient's cytokine polymorphism profile, i.e., allelic distribution, is then compared to controls. The controls are from patients who are periodontally healthy and from adult nonsevere periodontitis patients and adult severe periodontitis patients. That is, the patient's profile is compared to healthy people and patients with periodontal disease of different severity according to consensus clinical criteria and the match determines the predisposition towards periodontal disease. In one embodiment, controls are provided that are ethnically matched to accommodate genetic variations within subpopulations.

An odds ratio (approximate relative risk) is derived to test the association between allelic polymorphism pattern (genotype) at these specific loci and development of disease and/or its severity. This provides predictive information that will be used in the clinical management of periodontal disease.

The above discussion provides a factual basis for a kit for the identification of a patient's genetic polymorphism pattern associated with increased periodontal disease severity. The identification of those at risk for severe disease allows preventive measures to be initiated prior to disease onset. Further, those patients who have two risk factors, smoking and the susceptible genotype, can be particularly monitored since their risk of severe disease is extremely high. The methods used with and the utility of the present invention can be shown by the following example.

EXAMPLE

Polymorphism Determination and Disease Association

General Methods

Reactions and manipulations involving DNA techniques, unless stated otherwise, were performed as described in Sambrook et al., 1989, *Molecular Cloning: A Laboratory Manual*, Cold Spring Harbor Laboratory Press, incorporated herein by reference. Methodology as set forth in U.S. Pat. Nos. 4,666,828; 4,801,531; and 5,272,057 and McDowell et al., 1995 are also used unless stated otherwise.

Enzymes used in PCR were from GIBCO BRL, thermocyclers were either Perkin-Elmer or Biometra. Restriction enzymes NcoI and TaqI were from Promega (US). Restriction enzymes AvaI and Bsu36I were from NEB (US).

Patient Selection and Disease Classification

Genetic polymorphisms associated with periodontal disease in adults was determined using the protocol of McDowell et al. (1995). Because of the masking effect of smoking, genetic factors associated with severe disease were determined in nonsmokers. A group of otherwise healthy adults were screened at a dental clinic for the presence of periodontal disease. The study included primarily individuals of Northern European descent. Each patient was screened for the absence of disease or, if the disease was present, its degree in each of four parameters. The four variables of interest are clinical attachment loss (CAL), pocket depth, gingivitis and interproximal bone loss. A blood sample is taken, DNA isolated and the genetic polymorphism at IL-1A and IL-1B genetic loci determined. In addition, a dental history of each patient was obtained including specific questions on family history of diabetes, cardiovascular disease or early tooth loss as well as whether they were smokers.

In order to determine periodontal disease status, each patient underwent an examination including a full mouth measurement of pocket depth (PD), recession (R), plaque (Pl) and bleeding on probing (BOP). Clinical attachment loss (CAL) is computed from pocket depth and recession. Radiographs assess bone loss. Based on these measurements, the patient was classified as either healthy, mild to moderate periodontitis or severe periodontitis.

All clinical variables were calculated on six surfaces (distal buccal, buccal, mesial buccal, mesial lingual, lingual and distal lingual) on each tooth (excluding third molars) for up to 168 sites. All radiographic variables were calculated on two surfaces on each tooth for up to 56 sites.

Disease severity classification is as follows:

Periodontally Healthy: Patients presented with all pocket depths $\leq 4$ mm, unlimited facial CAL, interproximal CAL of $\leq 2$ mm and <15% radiographic bone loss. Unlimited plaque and gingival inflammation and recession may be present.

Mild to Moderate Periodontitis: No history of disease onset prior to age 35. Patients presented with no more than two missing teeth, other than third molars, teeth extracted for orthodontic therapy and teeth lost as a result of extra-oral trauma. Patients also presented with a PD$\geq 6$ mm on five to nine interproximal sites. At least two of the qualifying interproximal sites must occur in different quadrants. Gingival inflammation (as exemplified by bleeding on probing) was present in at least two quadrants. Full mouth radiographs must disclose less than four interproximal sites with $\geq 50$% bone loss. Radiographic total mouth mean bone loss must be less than 25%. There is no specifications for CAL in this classification.

Severe Periodontitis: Patients presented with of $\geq 10$ interproximal sites that measure $\geq 7$ mm, with PD of $\geq 7$ mm occurring on at least eight teeth. CAL measured $\geq 5$ mm on $\geq 11$ sites. Full mouth radiographs taken within the last three years showed $\geq 7$ interproximal sites with $\geq 50$% bone loss on radiographs with a total mouth mean bone loss greater than 30%.

Statistical Analysis $\chi^2$ analysis was used. The Odds Ratio (relative risk) is calculated from a 2×2 contingency table as described by Woolf, 1955.

PCR Amplification and Restriction Enzyme Digestion Protocols for Selected Alleles

IL-1A

The single base variation (C/T) polymorphism at IL-1A base −889 was identified as follows:

SCREENING: PCR amplification of genomic templates. One mismatch inserted in a primer to complete an NcoI site if C is available at −889

PRIMERS: The following primers were produced in an ABI DNA synthesizer based on the genomic sequences (Furutani et al., 1986; GENBANK X03833).

5' TGT TCT ACC ACC TGA ACT AGG C 3'  
(−967/−945) (SEQ ID No:1)

5' TTA CAT ATG AGC CTT CCA TG 3'  
(−888/−869) (SEQ ID No:2)

PCR CONDITIONS:
[96° C. (1 minute)] 1 cycle;
[94° C. (1 minute), 46° C. (1 minute), 72° C. (1 minute)] 40 cycles;
[72° C. (4 minutes)] 1 cycle.

RESTRICTION ENZYME DIGESTION: Digestion was with NcoI at 37° C., for 8 hours. Sizing was by 8% PAGE or 2% agarose gels.

PREDICTED RESULTS FROM DIGESTION:

Allele 1 (C) NcoI digestion of PCR products of allele 1 will yield 83 and 16 basepair (bp) fragments.

Allele 2 (T) NcoI digestion of PCR products of allele 2 will be ineffective and yield a 99 basepair (bp) product.

IL-1B (AvaI)

The single base variation (C/T) polymorphism at IL-1B base −511 was identified as follows:

SCREENING: PCR amplification of genomic templates. The single base variation completes an AvaI site on allele 1 (C), a Bsu36I site on allele 2 (T).

PRIMERS: The following primers were produced in an ABI DNA synthesizer based on the genomic sequences (Clark et al., 1986; GENBANK X04500).

5' TGG CAT TGA TCT GGT TCA TC 3'  
(−702/−682) (SEQ ID No:3)

5' GTT TAG GAA TCT TCC CAC TT 3'  
(−417/−397) (SEQ ID No:4)

PCR CONDITIONS:
[95° C. (2 minutes)] 1 cycle;
[95° C. (1 minute), 53° C. (1 minute), 74° C. (1 minute)] 35 cycles;
[74° C. (4 minutes)] 1 cycle.

RESTRICTION ENZYME DIGESTION: Digestion was at 37° C., for 8 hours. Sizing was by 8% PAGE.

PREDICTED RESULTS FROM DIGESTION:

Allele 1 (C) AvaI digestion of PCR products of allele 1 will yield 190 and 114 bp fragments. Bsu36I digestion of PCR products of allele 1 will be ineffective and yield a 304 bp product.

Allele 2 (T) AvaI digestion of PCR products of allele 2 will be ineffective and yield a 304 bp product. Bsu36I digestion of PCR products of allele 2 will yield 190 and 114 bp fragments.

In-1B (TaqI)

The single base variation (C/T) polymorphism at IL-1B base +3953 was identified as follows:

SCREENING: PCR amplification of genomic templates. One mismatch was inserted in a primer to complete a TaqI site as a positive control. Polymorphic TaqI site is native.

PRIMERS: The following primers were produced in an ABI DNA synthesizer based on the genomic sequences (Clark et al., 1986; GENBANK X04500).

5' CTC AGG TGT CCT CGA AGA AAT CAA A 3'  
(+3844/+3868) (SEQ ID No:5)

5' GCT TTT TTG CTG TGA GTC CCG 3'  
(+4017/+4037) (SEQ ID No:6)

PCR CONDITIONS:
[95° C. (2 minutes)] 1 cycle;
[95° C. (1 minute), 67.5° C. (1 minute), 74° C. (1 minute)] 38 cycles;
[72° C. (8 minutes)] 1 cycle.

RESTRICTION ENZYME DIGESTION: Digestion was at 60° C., for 8 hours. Sizing was by 8% PAGE.

PREDICTED RESULTS FROM DIGESTION:

Allele 1 (C) TaqI digestion of PCR products of allele 1 will yield 12, 85 and 97 bp fragments.

Allele 2 (T) TaqI digestion of PCR products of allele 2 will yield 12 and 182 bp fragments.

RESULTS

Adults, smokers and nonsmokers, were screened for periodontal disease severity using a consensus clinical criteria as described herein above. The data are shown in Table 1.

TABLE 1

| Group | H | | M | | S | |
|---|---|---|---|---|---|---|
| N | 49 | | 42 | | 42 | |
|  | mean | S.D. | mean | S.D. | mean | S.D. |
| BOP * | 10.44 | 7.77 | 20.84 | 10.91 | 26.37 | 13.63 |
| PD | 2.84 | 0.49 | 3.85 | 0.3 | 4.31 | 0.46 |
| CAL | 2.68 | 0.89 | 4.31 | 0.5 | 8.66 | 1.33 |
| # > 49% | 0 | 0 | 0.48 | 0.67 | 14.8 | 7.6 |
| % bl | 11.8 | 2 | 22.4 | 2.6 | 41.8 | 8.3 |

Abbreviations used in Tables: PD (pocket depth), BOP (bleeding on probing), CAL (clinical attachment loss), #>49% (number of sites where bone loss is greater than 49%), % bl (percent bone loss), S.D. (standard deviation); H=healthy, M=mild/moderate, S=severe, * indicates significance at least at 95% confidence level.

In Table 2 the clinical data is displayed and compared between smokers and nonsmokers. Note that there is a significant difference in the overall clinical disease state between smokers and nonsmokers.

TABLE 2

| Smoke | No | | Yes | | P | |
|---|---|---|---|---|---|---|
| N | 100 | | 36 | | | |
|  | mean | S.D. | mean | S.D. | | |
| BOP | 17.4 | 11.9 | 22.85 | 0.14 | 0.042 | * |
| PD | 3.42 | 0.62 | 3.97 | 0.78 | 4E-04 | ** |
| CAL | 3.98 | 1.61 | 5.7 | 2.08 | 1E-04 | ** |
| N | 98 | | 35 | | | |
| # > 49% | 2.43 | 5.82 | 11.59 | 9.88 | 1E-04 | ** |
| % bl | 20.53 | 10.83 | 36.76 | 13.04 | 1E-04 | ** |

Abbreviations as in Table 1.

Table 3 summarizes and compares the clinical findings for IL-1A alleles 1 and 2. Allelic genotype for each gene is indicated by the paired numbers, i.e. 1/1 indicates homozygosity for allele 1, 1/2 indicates heterozygous for alleles 1 and 2, etc. Where the genotype is given as allele 2 this indicates at least one copy of the allele is present. The analysis is done with the non-smokers. As the data in Table 2 indicates, the smokers as a group had severe disease such that they are not included in the analysis for genetic predisposition. The data in Table 3 shows there is a significant association of severe clinical disease for the carriers of IL-1A allele 2 particularly for percent bone loss, CAL and PD. The population analyzed included all disease groups for nonsmokers.

TABLE 3

| IL-1A | 11 | | 12 or 22 | | | |
|---|---|---|---|---|---|---|
| N | 44 | | 54 | | | |
|  | mean | S.D. | mean | S.D. | p | |
| BOP | 16.7 | 12.7 | 18 | 11.6 | 0.598 | |
| PD | 3.28 | 0.65 | 3.36 | 0.58 | 0.58 | |
| CAL | 3.62 | 1.48 | 4.3 | 1.56 | 0.036 | * |
| # > 49% | 1.48 | 4.83 | 3.2 | 6.45 | 0.133 | |
| % bl | 17.41 | 8.77 | 23.19 | 11.36 | 0.006 | ** |

Abbreviations as in Table 1.

In Table 4, the same analysis is performed for IL-1B(TaqI) alleles 1 and 2.

TABLE 4

| IL-1B (TaqI) | 11 | | 12 or 22 | | |
|---|---|---|---|---|---|
| N | 51 | | 47 | | |
|  | mean | S.D. | mean | S.D. | p |
| BOP | 18.3 | 12.1 | 18.6 | 12 | 0.341 |
| PD | 3.35 | 0.56 | 3.5 | 0.67 | 0.234 |
| CAL | 3.82 | 1.44 | 4.18 | 1.79 | 0.278 |
| # > 49% | 1.73 | 6.07 | 3.18 | 6.5 | 0.218 |
| % bl | 18 | 9.14 | 22.32 | 11.9 | 0.123 |

Abbreviations as in Table 1.

In Table 5, the same analysis is presented for patients who have (+) the genotype IL-1A allele 2 plus IL-1B (TaqI) allele 2 versus those who do not (−). More specifically, the −genotype is IL-1A(1/1) plus IL-1B(TaqI) (1/1 or 1/2 or 2/2) OR IL-1A (1/2 or 2/2) plus IL-1B(TaqI)(1/1). The + genotype is IL-1A (1/2 or 2/2) plus IL-1B(TaqI)(1/2 or 2/2).

TABLE 5

| Genotype | − | | + | | | |
|---|---|---|---|---|---|---|
| N | 63 | | 35 | | | |
|  | mean | S.D. | mean | S.D. | p | |
| BOP | 16.2 | 12.0 | 19.5 | 11.9 | 0.194 | |
| PD | 3.32 | 0.59 | 3.62 | 0.64 | 0.023 | * |
| CAL | 3.7 | 1.41 | 4.52 | 1.83 | 0.026 | * |
| # > 49% | 1.43 | 4.60 | 4.22 | 7.26 | 0.044 | * |
| % bl | 18.13 | 8.74 | 25.03 | 12.3 | 0.005 | ** |

Abbreviations as in Table 1.

The allelic distribution for IL-1A and IL-1B (TaqI) according to patient disease severity were determined and are shown in Table 6.

TABLE 6

| ALL SUBJECTS | | | | |
|---|---|---|---|---|
| Patient Genotype | | Disease Severity Distribution* | | |
| IL-1A | IL-1B (TaqI) | Healthy | Mild-Mod Disease | Severe Disease |
| 1/1 | 1/1, 1/2, 2/2 | 30<br>61.2% | 16<br>38.1% | 19<br>44.2% |
| 1/2, 2/2 | 1/1 | 8<br>16.3% | 10<br>23.8% | 8<br>18.6% |
| 1/2, 2/2 | 1/2, 2/2 | 11<br>22.4% | 16<br>38.1% | 15<br>35.7% |
|  |  | 49<br>100% | 42<br>100% | 42<br>100% |

*Distribution is given in both numbers of patients in each category and percent of patients for that disease category.

In Table 7, the results for nonsmokers for IL-1A and IL-1B(TaqI) is presented. Of patients with severe disease, 64.7% had a genotype of IL-1A 1/2 or 2/2 and IL-1B(TaqI) 1/2 or 2/2 indicating that the presence of allele 2, either in a heterozygous or homozygous genotype, leads to severe disease susceptibility.

TABLE 7

NONSMOKERS

| Patient Genotype | | | Disease Severity Distribution | |
|---|---|---|---|---|
| IL-1A | IL-1B (TaqI) | Healthy | Mild-Mod Disease | Severe Disease |
| 1/1 | 1/1,1/2, 2/2 | 27 61.4% | 13 35.2% | 4 23.5% |
| 1/2, 2/2 | 1/1 | 7 15.9% | 1 27.0% | 2 11.8% |
| 1/2, 2/2 | 1/2, 2/2 | 10 22.7% | 14 37.8% | 11 64.7% |
| | | 44 100% | 37 100% | 17 100% |

An odds ratio (approximate relative risk) was derived for the association between allelic polymorphism pattern (genotype) at IL-1A allele 2 and IL-1B (TaqI) allele 2 and development of disease and/or its severity. The Odds Ratio is calculated by using a Contingency Table as shown in Table 8. The following formula: (A×D)/(C×B) is used to calculate the Odds Ratio (Woolf, 1955).

TABLE 8

Sample Contingency Table

| Genotype of Interest | Phenotype 1 | Phenotype 2 |
|---|---|---|
| Present | A | B |
| Absent | C | D |

As shown in Table 9, patients who are smokers or who have the genotype IL-1A allele 2 plus IL-1B(TaqI) allele 2 (+ genotype) are more likely than those who do not have this genotype to have severe disease; they have an Odds Ratio of 10.06:1. Among nonsmokers only (Table 10) the Odds Ratio is 4.3:1 for those patients with the genotype IL-1A allele 2 plus IL-1B(TaqI) allele 2.

TABLE 9

Odds Ratio In All Subjects

| Smoker OR Genotype: IL-1A allele 2 plus IL-1B(TaqI) allele 2 | Severe Disease | Healthy or Mild-Mod Disease |
|---|---|---|
| PRESENT | 36 | 34 |
| Absent | 6 | 57 |

OR=10.06 (3.84–26.35)
$\chi^2$=26.95 (p<0.0001)

TABLE 10

Odds Ratio In Nonsmokers

| Genotype: IL-1A allele 2 plus IL-1B(TaqI) allele 2 | Severe Disease | Healthy or Mild-Mod Disease |
|---|---|---|
| PRESENT | 11 | 24 |
| Absent | 6 | 57 |

OR=4.3
$\chi^2$=7.53 (p=0.006)

The clinical data for the smoker or target genotype of IL-1A allele 2 plus IL-1B(TaqI) allele 2 (+ genotype) is shown in Table 11.

TABLE 11

| N | 63 mean | S.D. | 70 mean | S.D. | | |
|---|---|---|---|---|---|---|
| BOP | 16.24 | 12.01 | 21.01 | 12.98 | 0.0617 | ** |
| PD | 8.32 | 0.59 | 3.79 | 0.73 | 0.0008 | ** |
| CAL | 3.7 | 1.41 | 5.12 | 2.05 | 0.0001 | ** |
| # > 49% | 1.43 | 4.6 | 7.86 | 9.24 | 0.00001 | ** |
| % b1 | 18.13 | 8.74 | 30.32 | 13.68 | 0.00001 | ** |

Abbreviations as in Table 1.

The allelic distribution for IL-1A and IL-1B (AvaI) were determined for Nonsmokers (n=100) and is presented in Table 12. Of patients with severe disease, 36.8% had a genotype of IL-1A 1/2 or 2/2 and IL-1B(AvaI) 1/2 or 2/2.

TABLE 12

NONSMOKERS

| Patient Genotype | | | Disease Severity Distribution | |
|---|---|---|---|---|
| IL-1A | IL-1B (AvaI) | Healthy | Mild-Mod Disease | Severe Disease |
| 1/1 | 1/1, 1/2, 2/2 | 27 61.4% | 13 35.2% | 4 21.1% |
| 1/2, 2/2 | 1/1 | 11 25.0% | 10 27.0% | 8 42.1% |
| 1/2, 2/2 | 1/2, 2/2 | 6 13.6% | 14 37.8% | 7 36.8% |
| | | 44 100% | 37 100% | 19 100% |

Among nonsmokers only, the Odds Ratio is 0.85 for those patients with the genotype IL-1A allele 2 plus IL-1B(AvaI) allele 2 (Table 13). This genetic combination shows no association with periodontal disease severity.

TABLE 13

Odds Ratio In Nonsmokers

| Genotype: IL-1A allele 2 plus IL-1B(AvaI) allele 2 | Severe Disease | Healthy or Mild-Mod Disease |
|---|---|---|
| PRESENT | 10 | 46 |
| Absent | 9 | 35 |

The data presented show that of those subjects with severe disease 86.0% were either current smokers or had the target genotype IL-1A allele 2 plus IL-1B(TaqI) allele 2. Of the subjects who were neither current smokers nor had the target genotype, 90.5% did not have severe disease. Of the subjects who were either current smokers or had the target genotype, 52.1% had severe disease independent of any other risk factor.

The present invention therefore provides a method of identifying patients at risk for severe periodontal disease to allow early treatment.

Throughout this application various publications and patents are referenced. Full citations for the referenced publications and patents not included herein above are listed below. The disclosures of these publications in their entireties are hereby incorporated by reference into this application in order to more fully describe the state of the art to which this invention pertains.

The invention has been described in an illustrative manner, and it is to be understood that the terminology which has been used is intended to be in the nature of words of description rather than of limitation.

Obviously, many modifications and variations of the present invention are possible in light of the above teach-

REFERENCES

Blakemore et al., "Interleukin-1 receptor antagonist gene polymorphism as a severity factor in systemic lupus erythematosus" *Arthritis and Rheumatism* 37(9):1380–1385 (1994).

Clark et al., "Genomic sequence for human prointerleukin 1 beta: possible evolution from a reverse transcribed prointerleukin 1 alpha gene" *Nucl Acids Res* 14:7897–7914 (1986) [published erratum appears in *Nucleic Acids Res* 15(2):868 (1987)].

de Giovine et al., "Single base polymorphism at −511 in the human interleukin-1β gene (IL1β)" *Human Molecular Genetics* 1, No. 6:450 (1992).

Duff, "Cytokines and anti-cytokines" *Br. J. Rheumatol* 32 (Suppl 1):15–20 (1993).

Furutani et al., "Complete nucleotide sequence of the gene for human interleukin 1 alpha" *Nucl Acids Res* 14:3167–3179 (1986).

Mansfield et al., "Novel genetic association between ulcerative colitis and the anti-inflammatory cytokine interleukin 1 receptor antagonist" *Gastroenterology* 106:637–642 (1994).

McDowell et al., "A genetic association between juvenile rheumatoid arthritis and a novel interleukin-1 alpha polymorphism" *Arthritis & Rheumatism* (in press 1995).

McGuire et al., "Variation in the TNF-α promoter region associated with susceptibility to cerebral malaria" *Nature* 371:508–511 (1994).

Michalowicz et al., "Periodontal findings in adult twins" *J Periodontol* 62:293–299 (1991)

Basic and Clinical Immunology, 8th Ed. eds Stites, Terr & Parslow, Chapter 9, pgs 105–123.

Verjans et al., "Polymorphism of the tumor necrosis factor region in relation to disease: An overview" *Rheum Dis Clin North Am* 18:177–186 (1992).

Wilson et al., "Single base polymorphism in the human Tumor Necrosis Factor alpha (TNFα) gene detectable by Nco1 restriction of PCR product" *Human Molecular Genetics* 1, No. 5:353 (1992).

Woolf, B., "Estimating the relationship between blood groups and disease" *Annals of Human Genetics* 19:251–253 (1955).

---

We claim:

1. A method of predicting a patient's susceptibility to increase periodontal disease severity, comprising the steps of:

(a) isolating genomic DNA from a patient;
    (b) determining a genetic polymorphism pattern for IL-1A and IL-1B in the genomic DNA; and
    (c) comparing the genetic polymorphism patterns to a control sample, wherein said control sample comprises an IL-1A allele 2 plus an IL-1B (Taq 1) allele 2, and wherein the similarity of the genetic polymorphism pattern to the control sample indicates susceptibility to increased periodontal disease severity.

2. The method as set forth in claim 1 wherein the control samples are ethnically matched control samples of known disease severity.

3. The method as set forth in claim 1 wherein said step for identifying in the DNA a genetic polymorphism pattern for IL-1A and IL-1B includes amplification of target DNA sequences using the polymerase chain reaction (PCR) wherein the PCR primers used are:

5' TGT TCT ACC ACC TGA ACT AGG C 3';   (SEQ ID No:1)

5' TTA CAT ATG AGC CTT CCA TG 3';   (SEQ ID No:2)

5' TGG CAT TGA TCT GGT TCA TC 3';   (SEQ ID No:3)

5' GTT TAG GAA TCT TCC CAC TT 3';   (SEQ ID No:4)

5' CTC AGG TGT CCT CGA AGA AAT CAA A 3';   (SEQ ID No:5)

and

5' GCT TTT TTG CTG TGA GTC CCG 3'.   (SEQ ID No:6)

4. The method as set forth in claim 1 wherein said step for identifying in the DNA a genetic polymorphism pattern for IL-1A and IL-1B includes restriction enzyme digestion with restriction enzymes NcoI, TaqI, AvaI and Bsu36I.

5. The method as set forth in claim 1, wherein the alleles known to be associated with increased disease severity comprise an IL-1A allele 2 plus an IL-1B(TaqI) allele 2.

6. A method of predicting a patient's susceptibility to severe periodontal disease, said method comprising the steps of:

a) isolating genomic DNA from a patient; and
    b) determining an allelic pattern for IL-1A and IL-1B in the genomic DNA;
        wherein the allelic pattern selected from the group consisting of
            at least one copy of IL-1A allele 2,
            at least one copy of IL-1B(TaqI) allele 2, and
            at least one copy of IL-1A allele 2 plus at least one copy of IL-1B(TaqI) allele 2
        indicates increased susceptibility to severe periodontal disease.

7. The method as in claim 6, wherein said step of determining an allelic pattern comprises amplification with a polymerase chain reaction (PCR) and at least one PCR primer, wherein said PCR primer is selected from the group consisting of:

5' TGT TCT ACC ACC TGA ACT AGG C 3';   (SEQ ID No:1)

5' TTA CAT ATG AGC CTT CCA TG 3';   (SEQ ID No:2)

-continued

5' TGG CAT TGA TCT GGT TCA TC 3';  (SEQ ID No:3)

5' GTT TAG GAA TCT TCC CAC TT 3';  (SEQ ID No:4)

5' CTC AGG TGT CCT CGA AGA AAT CAA A 3';  (SEQ ID No:5)

and

5' GCT TTT TTG CTG TGA GTC CCG 3'.  (SEQ ID No:6)

8. The method as in claim 6, wherein said step of determining an allelic pattern comprises digestion with at least one restriction enzyme selected from the group consisting of NcoI, TaqI, AvaI and Bsu36I.

9. A kit for predicting a patient's susceptibility to severe periodontal disease, said kit comprising:
(a) a DNA sample collecting means;
(b) a means for determining a genetic polymorphism pattern for IL-1A and IL-1B, wherein said means comprises a set of polymerase chain reaction (PCR) primers, wherein said primers consist of:

5' TGT TCT ACC ACC TGA ACT AGG C 3';  (SEQ ID No:1)

5' TTA CAT ATG AGC CTT CCA TG 3';  (SEQ ID No:2)

5' TGG CAT TGA TCT GGT TCA TC 3';  (SEQ ID No:3)

5' GTT TAG GAA TCT TCC CAC TT 3';  (SEQ ID No:4)

5' CTC AGG TGT CCT CGA AGA AAT CAA A 3';  (SEQ ID No:5)

and

5' GCT TTT TTG CTG TGA GTC CCG 3';  (SEQ ID No:6)

and (c) a control sample comprising IL-1A allele 2 and IL-1B (Taq I) allele 2.

* * * * *

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:1:

TGTTCTACCA CCTGAACTAG GC    22

(2) INFORMATION FOR SEQ ID NO:2:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:2:

TTACATATGA GCCTTCCATG    20

(2) INFORMATION FOR SEQ ID NO:3:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:3:

TGGCATTGAT CTGGTTCATC    20

(2) INFORMATION FOR SEQ ID NO:4:

(i) SEQUENCE CHARACTERISTICS:

(A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:4:

GTTAGGAAT CTTCCCACTT                                                                                20

(2) INFORMATION FOR SEQ ID NO:5:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:5:

CTCAGGTGTC CTCGAAGAAA TCAAA                                                                         25

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:6:

GCTTTTTTGC TGTGAGTCCC G                                                                             21